United States Patent
Yang et al.

(10) Patent No.: US 10,874,598 B2
(45) Date of Patent: Dec. 29, 2020

(54) COMPOSITIONS AND METHODS FOR TREATING DAMAGED HAIR

(71) Applicant: AVON PRODUCTS, INC., Rye, NY (US)

(72) Inventors: Sen Yang, Highland, NY (US); Allwyn Colaco, Morristown, NJ (US); Michael J. Fair, Ridgewood, NJ (US)

(73) Assignee: Avon Products, Inc., Suffern, NY (US)

( * ) Notice: Subject to any disclaimer, the term of this patent is extended or adjusted under 35 U.S.C. 154(b) by 23 days.

(21) Appl. No.: 15/801,832

(22) Filed: Nov. 2, 2017

(65) Prior Publication Data

US 2018/0116935 A1    May 3, 2018

Related U.S. Application Data

(63) Continuation of application No. 14/354,827, filed as application No. PCT/US2014/018983 on Feb. 27, 2014, now abandoned.

(60) Provisional application No. 61/774,132, filed on Mar. 7, 2013.

(51) Int. Cl.
    *A61K 8/46*      (2006.01)
    *A61Q 5/00*      (2006.01)
    *A61K 8/81*      (2006.01)
    *A61Q 5/12*      (2006.01)

(52) U.S. Cl.
    CPC .............. *A61K 8/46* (2013.01); *A61K 8/817* (2013.01); *A61K 8/8152* (2013.01); *A61Q 5/002* (2013.01); *A61Q 5/12* (2013.01); *A61K 2800/00* (2013.01)

(58) Field of Classification Search
    None
    See application file for complete search history.

(56) References Cited

U.S. PATENT DOCUMENTS

| 4,752,467 | A  | 6/1988  | Konrad et al.    |
| 4,855,130 | A  | 8/1989  | Konrad et al.    |
| 5,573,709 | A  | 11/1996 | Wells            |
| 5,785,959 | A  | 7/1998  | Wolf et al.      |
| 2003/0108507 | A1 | 6/2003 | Clipson et al.  |
| 2004/0067245 | A1 | 4/2004 | Mahalingam et al. |
| 2008/0112897 | A1 | 5/2008 | Schiemann et al. |
| 2008/0193401 | A1 | 8/2008 | Bell et al.     |

(Continued)

FOREIGN PATENT DOCUMENTS

| CH | 686285 A5      | 2/1996 |
| DE | 102010062615 A1 | 4/2012 |
| JP | 2008013549 A   | 1/2008 |

OTHER PUBLICATIONS

Hessefort et al., "True porosity measurement of hair: A new way to study hair damage mechanisms", J. Cosmet. Sci., 59, 303-315 (Jul./Aug. 2008). (Year: 2008).*

(Continued)

*Primary Examiner* — Carlos A Azpuru
*Assistant Examiner* — Casey S Hagopian
(74) *Attorney, Agent, or Firm* — Brian P. McCloskey

(57) ABSTRACT

Compositions and methods are disclosed for repairing damaged keratin fibers or otherwise strengthening keratin fibers, including hair of the human scalp, and particularly hair that has been damaged chemically, physically, thermally or by other means. The compositions comprise 3,3'-thiodipropionic acid (TDPA) or a derivative thereof in a cosmetically acceptable vehicle.

2 Claims, 1 Drawing Sheet

(56) References Cited

U.S. PATENT DOCUMENTS

| | | |
|---|---|---|
| 2010/0119461 A1 | 5/2010 | Bicard-Benhamou et al. |
| 2010/0172859 A1 | 7/2010 | Matsunaga et al. |
| 2010/0189664 A1* | 7/2010 | Castro .................... A61K 8/731 |
| | | 424/52 |
| 2011/0052517 A1 | 3/2011 | Santhanam et al. |
| 2013/0052288 A1 | 2/2013 | Leeson et al. |
| 2013/0064905 A1 | 3/2013 | Duggan et al. |

OTHER PUBLICATIONS

Lansdown, Alan B. G. "Hair Dyes and Hair Treatments" May 5, 2006 accessed at www.chemistryexplained.com on Jun. 22, 2015.

Lee et al. "Hair Shaft Damage from Heat and Drying Time of Hair Dryer", Ann Dermatol 23(4) 455-462, 2011.

Screenshot of shampooing hair, "Beauty by Marbella in HD—How to properly shampoo, condition and towel dry your hair", published on Feb. 24, 2013, accessed atwww.youtube.com/watch?v=zoP8jhlJ4rE on Jan. 18, 2017.

Screenshot of towel drying hair, "Beauty by Marbella in HD—How to properly shampoo, condition and towel dry your hair", published on Feb. 24, 2013, accessed atwww.youtube.com/watch?v=zoP8jhlJ4rE on Jan. 18, 2017.

Screenshot of towel drying hair, "Men's Flair Styling Tips: How to Apply Hair Product", published on Jan. 11,2011, accessed at www.youtube.com/watch?v=m0DtavZOm3o on Jan. 18, 2017.

Screenshot of applying hair product, "Men's Hair Styling Tips: How to Apply Hair Product", published on Jan. 11, 2011, accessed at www.youtube.com/watch?v=m0DtavZOm3o on Jan. 18, 2017.

\* cited by examiner

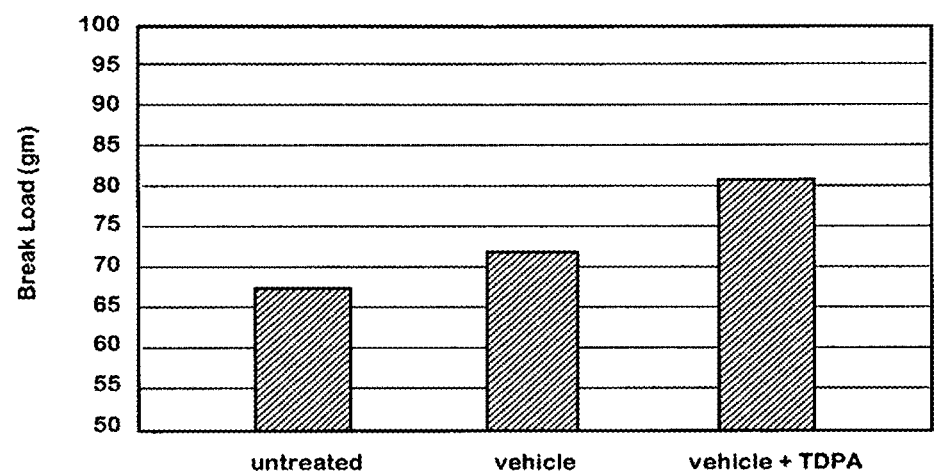

COMPOSITIONS AND METHODS FOR TREATING DAMAGED HAIR

CROSS-REFERENCE TO RELATED APPLICATIONS

This application is a Continuation of U.S. Ser. No. 14/354,827, filed Apr. 28, 2014, which claims priority benefit, under the national stage entry under 35 U.S.C. 371 of International Application No. PCT/US14/18983, filed on Feb. 27, 2014 the contents of which are hereby incorporated by reference in their entirety. This patent application claims priority to U.S. Patent Application Ser. No. 61/774,132, filed on Mar. 7, 2013. The entirety of the aforementioned applications are incorporated herein in their entirety by reference.

FIELD OF INVENTION

The present invention relates to methods and compositions for strengthening keratin fibers and for repairing damaged keratin fibers. In particular, the present invention relates to hair care compositions, such as shampoos and conditioners, that comprise effective amounts of 3,3'-thiodipropionic acid (TDPA) or a derivative thereof which strengthen and repair damaged hair of the scalp.

BACKGROUND OF THE INVENTION

A number of products and treatments are available to consumers to modify the appearance of human hair, including hair dyes, lighteners or bleaches, permanent treatments, and the like. Some of these treatments employ harsh chemicals or heat which may damage and weaken human hair. Even less harsh treatments, including blow drying or even brushing or combing or hair can cause damage over time. Exposure to excessive UV radiation from the sun and environmental insults, including chemicals in swimming pools, may likewise damage hair. The cumulative result of these factors is often dry, brittle hair that is prone to breaking or splitting.

There is a need for compositions which strengthen hair to prevent or remediate the effects of chemical, mechanical, and environmental damage. It is therefore an object of the invention to provide compositions, including shampoos and hair conditioners, which strengthen and repair damaged hair of the scalp. It is a further object of the invention to provide treatment regimens for preventing or remediating damage to the hair, particularly hair that has been artificially colored or lightened.

SUMMARY OF THE INVENTION

In accordance with the foregoing objectives and others, the present invention provides methods and compositions for preventing, reversing, remediating, and/or forstalling damage to human hair of the scalp, and in particular, hair which has been previously artificially colored or lightened. In one aspect of the invention, compositions are provided comprising, in a topically acceptable vehicle, effective amounts of compounds having the structure shown of Formula (I).

where X is selected from —O—, —S—, —CH$_2$—, —NH—, or —NR$^N$— (where R$^N$ is methyl or ethyl), but will typically be —S—, and R$_1$ and R$_2$ are independently selected from hydrogen, C$_{1-22}$ hydrocarbon radicals, and cations (e.g., ammonium, quaternary amines, alkali or alkali-earth metals, etc.). In some implementations, X is —S—, R$_1$ and R$_2$ are hydrogen, and the compound of Formula (I) is 3,3'-thiodipropionic acid (TDPA). In some embodiments, R$_1$ and/or R$_2$ are independently selected from C$_{1-20}$ hydrocarbon radicals. In some embodiments, R$_1$ and/or R$_2$ are independently selected from C$_{1-15}$ hydrocarbon radicals. In some embodiments, R$_1$ and/or R$_2$ are independently selected from C$_{1-10}$ hydrocarbon radicals. In some embodiments, R$_1$ and/or R$_2$ are independently selected from C$_{1-5}$ hydrocarbon radicals.

In one aspect of the invention, a hair care product is provided comprising an effective amount of a compound of Formula (I) (e.g., TDPA) in a topically acceptable vehicle, such as an aqueous solution or emulsion. In some implementations, the hair care product will be a hair conditioner that is either of the rinse-off or leave-in variety.

In other aspect, methods of treating the hair are provided, comprising applying a composition comprising and effective amount of a compound of Formula (I) (e.g., TDPA), to the hair at least once weekly, more typically at least once daily, for a period sufficient to show improvement in the strength of the hair (e.g., tensile strength, resistance to breaking, and/or fewer split ends, etc.) or the overall aesthetic appearance of the hair. The duration of treatment will typically be at least five days, more typically at least one or two weeks, or longer.

These and other aspects of the present invention will become apparent to those skilled in the art after a reading of the following detailed description of the invention, including the appended claims.

BRIEF DESCRIPTION OF THE DRAWINGS

FIG. 1 illustrates the tensile load required to break hair fibers that were untreated, treated with vehicle, or treated with vehicle plus TDPA.

DETAILED DESCRIPTION

All amounts provided in terms of weight percentage are relative to the entire composition unless otherwise stated. Unless otherwise provided, the term "alkyl" is intended to embrace straight-chained, branched, or cyclic hydrocarbons, particularly those having from one to 20 carbon atoms, and more particularly C$_{1-12}$ hydrocarbons.

As used herein, the term "keratin fiber" includes hair of the scalp, eyelashes, eyebrows, facial hair, and body hair such as hair of the arms, legs, etc. Keratin fibers are not limited to humans and also include any keratin fibers from a mammal, such as, for example, pet hair and mammalian fur.

The compounds of the invention will generally have the structure shown of Formula (I).

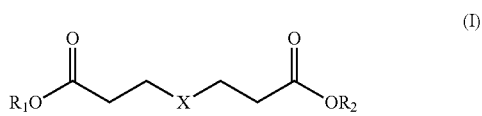

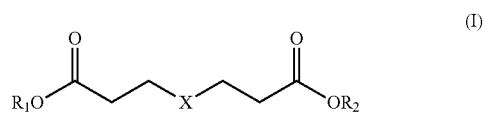

In the compounds of Formula (I), X is selected from —O—, —S—, —CH$_2$—, —NH—, or —NR$^N$— (where R$^N$ is methyl or ethyl), but will typically be —S—.

Generally, R$_1$ and R$_2$ are independently selected from hydrogen, C$_{1-22}$ hydrocarbon radicals, and cations (e.g., ammonium, quaternary amines, alkali or alkali-earth metals, etc.). In some embodiments R$_1$ and/or R$_2$ are hydrogen. In the case where R$_1$ and R$_2$ are hydrogen, the compound of Formula (I) is 3,3'-thiodipropionic acid (TDPA). Salts of TDPA are also contemplated including the case where one or both of the carboxylic acids are ionized. Cosmetically acceptable counterions (i.e., cations) usually, but not necessarily, are formed by the acid addition reaction with pH adjusters such as sodium hydroxide, triethanolamine, and the like.

In some embodiments, R$_1$ and/or R$_2$ are C$_{1-22}$ hydrocarbon radicals, including, without limitation, alkyl, alkenyl (e.g., vinyl, allyl, etc.), alkynyl, aryl (e.g., phenyl), alkyl-aryl (e.g., benzyl), aryl-alkyl (e.g., methylphenyl), heteroaryl, and combinations thereof. The C$_{1-22}$ hydrocarbon radicals may be substituted with 1-10 heteroatoms, such as halogen, oxygen, nitrogen, and sulfur. Therefore, R$_1$ and R$_2$ may include halo (perfluoro, etc.), hydroxyl, alkoxy, epoxy, carboxy, oxa, oxo, ether, ester, amino, or amide groups, to name a few, including, without limitation, groups of the form —(RO)$_n$— where R is ethyl or propyl and n is an integer from 1 to 10, and the like. In one embodiment, R$_1$ and/or R$_2$ is an alkyl or alkenyl group (linear, branched, or straight chained) having from 1-22 carbon atoms, or from 2-18 carbon atoms, including, without limitation, C$_8$ (e.g., capryl), C$_{10}$ (e.g., capric), C$_{12}$ (e.g., lauryl), C$_{14}$ (e.g., myristyl), C$_{16}$ (e.g., cetyl), C$_{18}$ (e.g., stearyl), C$_{20}$ (e.g., arachidyl), and C$_{22}$ (e.g., behenyl) alkyl or alkenyl groups. In one embodiment, R$_1$ and/or R$_2$ are lauryl groups. The compounds may be mono-esters or TDPA (or a salt) or di-ester of TDPA.

3,3'-thiodipropionic acid (TDPA) is the compound of Formula (I) where X is —S— and R$_1$ and R$_2$ are each hydrogen. The other compounds of Formula (I) are referred to herein as "derivatives" of 3,3'-thiodipropionic acid (TDPA). Only those derivatives that are safe for contact with human integuments are considered appropriate for use in accordance with the invention.

The compositions will usually comprise a compound of Formula (I) (such as TDPA) in an amount from about 0.1% to about 5% by weight of the total composition. More typically, the compositions will comprise a compound of Formula (I) (e.g., TDPA) in an amount from about 0.25% to about 2.5% by weight or from about 0.5 to about 1.5% by weight of the total composition. In one embodiment, the compositions will comprise a compound of Formula (I) (e.g., TDPA) in an amount form about 0.75% to about 1.25% or about 1% by weight of the total composition.

The compositions may further comprise additional agents that impart strength to the hair, including, without limitation amino acids, creatine, cysteine, and ceramides, to name a few. Alternatively, the compositions may be free of additional hair strengthening ingredients. In some embodiments, the compositions will further comprise creatine, for example, in an amount from about 0.01 to about 5% by weight. In other embodiments, the compositions will be essentially free of creatine, by which is meant that the amount of creatine is insufficient to impart a measurable improvement in hair strengthening. In other embodiments, the compositions will be free of creatine.

The inventive compositions will typically comprise a topically acceptable vehicle. By "topically acceptable" is meant that the vehicle is safe for contact with a human integument. The vehicle may comprise a liquid, comprising a single phase, a dual-phase system, or an emulsion. The compositions can be aqueous or anhydrous, but will typically be in the form of an aqueous solution, dispersion, or emulsion, such as a water-in-oil, oil-in-water, silicone-in-water, water-in-silicone, or multiple emulsion, or the like. When formulated as an emulsion, an emulsifier or a stabilizer is typically included. Where the product is intended as a spray, it may be desirable to employ a single phase vehicle, or a dual phase vehicle comprising an aqueous phase and an oil phase, the oil phase comprising a silicone oil.

In one embodiment, the vehicle comprises a volatile solvent. Typically, a volatile solvent may have a vapor pressure of above about 0.01 mmHg at 20° C. Volatile solvents may include water, volatile C$_{5-12}$ hydrocarbons (e.g., isododecane), volatile silicones (e.g., cyclopentasiloxane), lower alcohols (e.g., ethanol, isopropyl alcohol, etc.), and the like. The volatile solvents may comprise up to about 99% (w/w) of the composition, more typically up to about 85% (w/w) of the composition.

The compositions may comprise and oil or an oil-containing phase may be composed of a singular oil or mixtures of different oils. Suitable non-limiting examples include vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Non-volatile silicone oils will include polydimethylsiloxanes and other polyalkylsiloxancs, polyarylsiloxanes, polyalkylarylsiloxanes, or mixtures thereof. The non-volatile silicone oils will typically have a viscosity from about 10 to about 60,000 centistokes at 25° C. and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

The compositions may include natural or synthetic filmforming polymers, including, without limitation, those that assist in styling and setting hair. Such natural polymers include shellac, alginates, gelatines, pectines, chitosan salts, and cellulose derivatives. Synthetic polymers that can be used are, for example, polyvinylpyrrolidone, polyvinyl acetate, polyacryl compounds such as acrylic acid or methacrylic acid polymers, basic polymers of esters of these two acids with aminoalcohols or the salts or quarternization products of these basic polymers, polyacrylnitrile, and copolymers of such compounds, for example, polyvinylpyrrolidone vinyl acetate or polyvinylpyrrolidone dimethylaminoethylmethacrylate. Other polymeric film formers include polyolefins, polyvinyls, polacrylates, polyurethanes, silicone elastomers, silicone resins, silicone-polyalkylene oxide copolymers, silicone acrylates, polyamides, polyesters, fluoropolymers, polyethers (e.g., PEG, PPG, and copolymers), polyacetates, polycarbonates, polyimides, rubbers (e.g., di- and tri-block copolymer elastomers or styrene, ethylene, propylene, and/or butylene), epoxies, formaldehyde resins, and homopolymers and copolymers of and of the foregoing.

Other suitable polymeric film formers include silicone polymers, acrylates, alkyl acrylates, polyurethanes, fluoropolymers such as Fluomer (polyperfluoroperhydrophenanthrene) and silicone acrylates such as acrylates/dimethicone copolymers sold under the trade names KP-545 or KP 550 (Shin-Etsu). Suitable film formers include, but are not limited to, Amino Bispropyl Dimethicone, Aminopropyl Dimethicone, Amodimethicone, Amodimethicone Hydroxystearate, Behenoxy Dimethicone, $C_{30-45}$ Alkyl Dimethicone, $C_{24-28}$ Alkyl Dimethicone, $C_{30-45}$ Alkyl Methicone, Cetearyl Methicone, Cetyl Dimethicone, Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone. Particularly preferred are silicone polymers, including Methicone (as described by CTFA Monograph No. 1581, which is incorporated herein by reference), Dimethicones (as described by CTFA Monograph No. 840, which is incorporated herein by reference) and Amodimethicones as described by CTFA Monograph No. 189, which is incorporated herein by reference).

In one embodiment, the film forming polymer is a silicone acrylate, such as that having the CTFA Monograph No. 10082 and the INCI name Acylates/Dimethicone. This polymer is commercially available from ShinEtsu Chemical Co., Ltd. under the trade name KP-544. In another embodiment, the film forming polymer may be a silicone urethane, such as that having the INCI Name Bis-Hydroxypropyl Dimethicone/SMDI Copolymer and the INCI Monograph ID No. 22006. This polymer is commercially available from Siltech Corp. under the trade name SILMER UR-5050, which comprises the polymer in Isododecane.

In some embodiments, it may be desirable to add a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc.

The compositions may comprise a cationic polymer. Cationic polymers include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. When present, the cationic polymer will typically comprise an amount of about 0.1% to about 15% (w/w) of the composition. In other embodiments the compositions may contain an amount of cationic (quaternium) ingredients that are anhydrous or have very low level of water, e.g., less than 1% by weight. Other suitable quaternium compounds include, without limitation, Polyquaternium-37 (INCI), Silicone Quaternium-18 (INCI), PEG-2 Dimeadowfoamamidoethylmonium Methosulfate and Hexylene Glycol (INCI), and Cetrimonium Chloride (INCI), to name a few. Such quaternium compounds, if present, will typically comprise from about 0.05% to about 5% by weight of the total composition, and more typically, from about 0.1% to about 1.5% by weight.

The compositions may also comprise monomer quaternary ammonium compounds such as, for example, alkyltrimethylammonium chlorides, dialkylmethyl-ammonium chlorides, alkyldimethylbenzylammonium chlorides, and alkylpyridinium chlorides.

In one embodiment, the composition comprises at least one hair conditioning agent selected from the group consisting of polyquaterniums, cationic polymers, cationic surfactants, non-volatile dimethicone oils, dimethiconols, amodimethicones, ester oils, fatty alcohols, cationic gums and cellulosics, amidoamines, cetrimonium chloride, behentrimonium chloride, stearamidopropyl dimethylamine, polyesteramines, and cationically charge-modified polymers derived from guar gum, cellulose, proteins, polypeptides, chitosan, lanolin, starches and amino silicones.

The compositions may include a nonionic surfactant such as Laureth-23, Ceteth-10, Ceteth-20, IsoCeteth-20, Steareth-20, Oleth-10, Oleth-20, or alkyl polyglucose. The nonionic surfactant may be formed from a fatty alcohol, a fatty acid, or a glyceride with a C8 to C24 carbon chain.

The compositions of the invention can further comprise proteins, peptides, and amino acids including hydrolyzed soy protein, lauryldimonium hydrolyzed soy protein (cationic Soya protein), wheat amino acids, corn, wheat, milk, or silk proteins, collagens, keratins, taurine and arginine hydrochloride, etc.

The composition may also comprise polyols (e.g., glycols), such as glycerin, propylene glycol, ethoxydiglycol, glycerin, butylene glycol, pentylene glycol, hexylene glycol, caprylyl glycol, and the like. These will typically be added in amount from about 0.001 to about 5% by weight.

The compositions may further include an emulsifier. The amount of emulsifier will typically be from about 0.001 to about 10% by weight, but preferably will range from about 0.01 to about 5% by weight, and most preferably about 0.1 to about 1% by weight, based upon the total weight of the composition.

The emulsifier may be of the polyethoxylated type (e.g., polyoxyethylene ethers or esters) comprising chains of the form —$(CH_2CH_2O)_n$—. Propoxylated emulsifiers are also contemplated to be suitable. Emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few.

Water-in-silicone emulsions are typically emulsified with a nonionic surfactant (emulsifier). Suitable emulsifiers include polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising —$(EO)_m$— and/or —$(PO)_n$— groups, where EO is ethyleneoxy and PO is 1,2-propyleneoxy, the side chains being typically capped or terminated with hydrogen or lower alkyl groups (e.g., $C_{1-6}$, typically $C_{1-3}$). In addition to the alkoxylated side chain, the silicone emulsifier may also comprise alkyl chains pendant from the silicone backbone. Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET™ series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Other examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

Additional emulsifiers are provided in the INCI Ingredient Dictionary and Handbook 11th Edition 2006, the disclosure of which is hereby incorporated by reference.

The compositions of the invention will typically have a pH ranging from 2-12, more typically from 2 to 10. In some embodiments, the compositions will have a pH ranging from about 3 to about 7, or from about 3.5 to about 6.5. The pH may be adjusted using conventionally acid or base pH adjusters including, without limitation, citric acid, mineral acids, ethanolamine and other amines, ammonia, sodium hydroxide, etc.

In some embodiments, it has been found desirable to include one or more agents that enhance the shine of hair treated with the compositions of the invention. The shine-enhancing agent may be, for example, lens-shaped particles such as hemi-spherical PMMA, including the hemi-spherical methyl methacrylate crosspolymer sold under the trade name 3D Tech PW (Plain) XP (Kobo). Other suitable shine enhancers include phenylpropyldimethylsiloxysilicate, polybutene, polyisobutene, hydrogenated polyisobutene. Silicone fluids, such as aryl-substituted siloxanes having high refractive indices are also useful as shine enhancers. Particular mention may be made of Phenyltrimethicone, which is available under the trade names SCI-TEC PTM 100 (ISP) and PDM20 (Wacker-Belsil), and Trimethylsiloxyphenyl Dimethicone (INCI name), which is available under the trade name PDM 1000 (Wacker-Belsil). The PDM20 material has a refractive index of 1.437 at 25° C. The PDM 1000 material has a refractory index of 1.461 at 25° C. Another suitable silicone fluid may be trimethylsiloxyphenyl dimethicone. In general, any aryl-substituted silicone having a refractive index of greater than 1.4 at 25° C. is contemplated to be suitable for restoring shine to hair treated with the inventive superhydrophobic materials. Phenyl silicones such as pentaphenyl trimethyl trisiloxane or tetraphenyl tetramethyl trisiloxane, commercially available as HRI fluids from Dow coming HRI, are also useful for enhancing shine. Certain organic compounds, such as octyl methoxy cinnamate, may also be used to enhance shine. The shine enhancer is typically present from about 0.01% to about 5% by weight of the total composition.

In addition to the foregoing, the compositions according to the invention may comprise pigments, pearlescents, and/or colorants to impart a desired color to the hair. Inorganic pigments include without limitation titanium dioxide, zinc oxide, iron oxides, chromium oxide, ferric blue, and mica; organic pigments include barium, strontium, calcium or aluminium lakes, ultramarines, and carbon black; colorants include without limitation D&C Green #3, D&C Yellow #5, and D&C Blue #1. Pigments and/or colorants may be coated or surface treated with one or more compatibilizers to aid in dispersion in the solvent. Preferred pigments and/or colorants are those surface treated to render them hydrophobic.

The compositions of the invention may optionally comprise other active and inactive ingredients typically associated with hair care products. The nature of these other ingredients and their amounts should preferably be suitable for formulating a stable hair care product which forms a film on keratin fibers. Preferably, these other ingredients include at least one bioactive ingredient for improving the keratin fiber. Suitable other ingredients include, but are not limited to, amino acids, antioxidants, chelating agents, colorants, emollients, emulsifiers, excipients, fillers, fragrances, gelling agents, humectants, minerals, moisturizers, photostabilizing agents (e.g., UV absorbers), preservatives, stabilizers, staining agents, surfactants, viscosity and/or rheology modifiers, vitamins, waxes and mixtures thereof. It is contemplated that the inventive hair care product of the present invention can also include anti-dandruff, deodorant, sunscreen and/or antiperspirant ingredients. Collectively, all such additional components usually will comprise less than 10% by weight of the composition.

The compositions typically comprises a preservative or anti-microbial agent, for example, methylchloroisothiazolinone, methylisothiazolinone, methylparaben, propylparaben, phenoxyethanol, or caprylyl glycol.

The composition of the present invention may be formulated in any suitable form, including various rinse-off and leave-in formulations, such as but not limited to shampoos, conditioners, serums, creams, sprays, emulsions, gels, balms, liquids, and the like.

In one embodiment, a leave-in conditioner comprises from 0.1 to about 2.5% by weight of a compound of Formula (I) (e.g., TDPA), from about 1% to about 97% by weight of a vehicle, and from about 0.01% to about 15% by weight (collectively) of one or more of the following: a conditioning agent, a thickener, an anionic, cationic, zwitterionic, or non-ionic surfactant, dimethicone oil, polyquaternium-37, panthenol, panthenyl ethyl ether, hydrogenated castor oil/sebacic acid copolymer, wheat amino acids, phytantriol, tocopheryl acetate, vinyl dimethicone/lauryl dimethicone crosspolymer, propylene glycol dicaprylate/dicaprate, phenoxyethanol, hydroxyethylcellulose, caprylyl glycol, PPG-1 Ttrideceth-6, and quaternium-80.

In one embodiment, a rinse off conditioner comprises from 0.1 to about 2.5% by weight of a compound of Formula (I) (e.g., TDPA), from about 1% to about 97% by weight of a vehicle, and from about 0.01% to about 15% by weight (collectively) of one or more of the following: a conditioning agent, a thickener, an anionic, cationic, zwitterionic, or non-ionic surfactant, cetyl alcohol, dimethiconol, cetearyl alcohol, stearamidopropyl dimethylamine, cetrimonium chloride, butylene glycol, glycol stearate, wheat amino acids, panthenyl ethyl ether, phytantriol, hydrogenated castor oil/sebacic acid copolymer, tocopheryl acetate, panthenol, vinyl dimethicone/lauryl/behenyl dimethicone crosspolymer, ceteareth-20, glycolic acid, and polyethylene glycol (including PEG-90M).

In one embodiment, a shampoo comprises from 0.1 to about 2.5% by weight of a compound of Formula (I) (e.g., TDPA), from about 1% to about 97% by weight of a vehicle, and from about 0.01% to about 15% by weight (collectively) of one or more of the following: a conditioning agent, a thickener, an anionic, cationic, zwitterionic, or non-ionic surfactant, lauryl glucoside, sodium laureth sulfate, cocamide MIPA, sodium lauroyl sarcosinate, glycol distearate, dimethicone, wheat amino acids, panthenyl ethyl ether, phytantriol, hydrogenated castor oil/sebacic acid copolymer, tocopheryl acetate, panthenol, vinyl dimethicone/lauryl/behenyl dimethicone crosspolymer, PEG-150 pentaerythrityl tetrastearate, guar hydroxypropyltrimonium chloride, citric acid, PEG-6 caprylic/capric glycerides, PPG-12-Buteth-16, and Acrylates/C10-30 Alkyl Acrylate Crosspolymer.

The compositions are advantageously applied to hair in need thereof, by which is meant hair that has been damaged, such as hair damaged by chemical (color treatments, perms, etc.), thermal (blow dryers, curling irons, etc.), or mechanical (combing and brushing, etc.) insults. Hair in need thereof may also include hair that is damaged by UV light and swimming pool chemicals. In one embodiment, the composition is applied to hair that has been previously artificially colored, for example, with a two-part oxidative dye.

The compositions are typically applied to wet hair, or to damp hair (such as hair that has been towel-dried), or to dry hair. The composition may be left on the hair, meaning that after application no immediate (e.g., within an hour of application) steps are taken to remove the composition (other than allowing volatile constituents to evaporate). The compositions may also be other rinse-off variety, including shampoos and conditioners, which are intended to be removed substantially contemporaneous with their application (e.g., within 30 minutes). Other products, including pomades, hair gels and mousses, sprays, and the like are also contemplated.

The compositions are typically applied for a time sufficient to improve the strength or overall appearance of the hair. This typically entails application daily for at least three days, at least five days, at least, one week, or at least two weeks, although it is expected that results may be seen after one use. In some embodiments, the compositions are applied to damp hair after (e.g., within 30 minutes) of shampooing. In some embodiments, the compositions are applied to damp hair after (e.g., within 30 minutes) of dying the hair, including with a two part oxidative dye.

EXAMPLE 1

This Example demonstrates that TDPA repairs damaged hair fibers as evidenced by an improvement in the tensile breaking strength of hair fibers treated with TDPA. A commercial rinse-off conditioner formulation was used as a control vehicle for the study. An active formulation was prepared by adding 1% (w/w) of TDPA to the control vehicle. Three samples of treated hair were prepared: untreated, treatment with the control vehicle, and treatment with the control vehicle plus 1% TDPA. The treatments were applied to hair tresses that had been previously damaged by artificially color with an oxidative dye. The treatments were repeated five times. The overall condition of the hair fibers was determined by measuring the tensile load required to break the fibers and the results of 30 fibers were averaged. The results are shown in FIG. 1. Untreated hair had a break load of about 68 gm whereas hair treated with the control vehicle (itself a damage repair product) showed modest improvement over untreated hair, having a break load of about 73 gm. In stark contrast, the active formula, having 1% TDPA, gave a break load of about 82 gm. This correlates to an improvement in the tensile strength of about 20%. The formulas used in the testing protocol were as follows:

Control Vehicle Formula:

DEMINERALIZED WATER
BUTYLENE GLYCOL
PANTHENOL-DL
METHYLPARABEN
CETRIMONIUM CHLORIDE/ISOPROPANOL
PEG-90M
CETYL ALCOHOL
CETEARYL ALCOHOL/CETEARETH-20
STEARAMIDOPROPYL DIMETHYLAMINE
ETHYLENE GLYCOL MONOSTEARATE
PROPYLPARABEN
WHEAT AMINO ACIDS-AQ. PRES
PHENOXYETHANOL
DIMETHIDCONOL
HYDROGENATED CASTOR OIL/SEBACIC ACID COPOLYMER
FRAGRANCE
GLYCOLIC ACID
VINYL DIMETHICONE/LAURYL DIMETHICONE CROSSPOLYMER - LIQUID
PANTHENYL ETHYL ETHER
TOCOPHERYL ACETATE-SYN
PHYTANTRIOL

Control Vehicle Formula+1% TDPA:

DEMINERALIZED WATER
BUTYLENE GLYCOL
PANTHENOL-DL
METHYLPARABEN
CETRIMONIUM CHLORIDE/ISOPROPANOL
PEG-90M
CETYL ALCOHOL
CETEARYL ALCOHOL/CETEARETH-20
STEARAMIDOPROPYL DIMETHYLAMINE
ETHYLENE GLYCOL MONOSTEARATE
PROPYLPARABEN
WHEAT AMINO ACIDS-AQ. PRES
PHENOXYETHANOL
DIMETHICONOL
HYDROGENATED CASTOR OIL/SEBACIC ACID COPOLYMER
FRAGRANCE
GLYCOLIC ACID
VINYL DIMETHICONE/LAURYL DIMETHICONE CROSSPOLYMER - LIQUID
PANTHENYL ETHYL ETHER
TOCOPHERYL ACETATE-SYN
3,3'-THIODIPROPIONIC ACID
PHYTANTRIOL

What is claimed is:

1. A method of improving the tensile strength of a keratin fiber comprising applying to a keratin fiber in need thereof a composition comprising, in a topically acceptable vehicle, an effective amount of

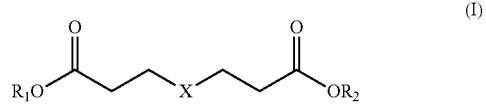

(I)

3,3'-thiodipropionic acid (TDPA) in an amount from about 0.75% to about 1.25% by weight of said composition; for a time sufficient to improve the tensile strength of said keratin fibers, wherein said keratin fibers are hair of the human scalp, wherein said keratin fibers have been previously artificially colored with an oxidative dye, and wherein the improvement in tensile strength is about 20%.

2. The method according to claim 1, wherein said keratin fibers have been damaged by chemical, thermal, or mechanical insults.

* * * * *